US00PP34555P2

(12) United States Plant Patent
Shoup

(10) Patent No.: US PP34,555 P2
(45) Date of Patent: Sep. 13, 2022

(54) SHRUB ROSE PLANT NAMED '1000 WISHES'

(50) Latin Name: *Rosa hybrida*
Varietal Denomination: 1000 Wishes

(71) Applicant: George Michael Shoup, Brenham, TX (US)

(72) Inventor: George Michael Shoup, Brenham, TX (US)

( * ) Notice: Subject to any disclaimer, the term of this patent is extended or adjusted under 35 U.S.C. 154(b) by 0 days.

(21) Appl. No.: 17/484,878

(22) Filed: Sep. 24, 2021

(51) Int. Cl.
*A01H 5/02* (2018.01)
*A01H 6/74* (2018.01)

(52) U.S. Cl.
USPC ..... Plt./107

(58) Field of Classification Search
USPC ..... Plt./101, 102, 107
See application file for complete search history.

*Primary Examiner* — Karen M Redden

(57) ABSTRACT

A new and distinct variety of shrub rose plant, herein referred to by its cultivar name, '1000 Wishes', is provided which abundantly, substantially, and continuously forms large single coral-pink colored blooms. The growth habit is rounded and bushy. The foliage is smooth, and dark green with a glossy finish. The plant propagates from cuttings easily, has a unique bloom color combination of both purple and yellow. The new variety is well suited to growing as attractive ornamentation and a source of fragrance in in the landscape.

1 Drawing Sheet

Botanical/commercial classification: Latin name—*Rosa hybrida.*

Varietal denomination: '1000 Wishes'.

SUMMARY OF THE INVENTION

The new variety of *Rosa hybrida* shrub rose plant was created at Brenham, Tex., U.S.A., by artificial pollination wherein two parents were crossed which previously had been observed in the hope that each would contribute their desired traits. The female parent (i.e., the seed parent) was a non-patented seedling derived from the varieties 'Bucbi' (U.S. Plant Pat. No. 4,225), 'Old Blush' (non-patented), and *Rosa wichuriana* 'Thornless' (non-patented). The male parent (i.e., the pollen parent) was the 'Miracle on the Hudson' variety (non-patented). The parentage of the new variety can be summarized as follows:

['Bucbi' x ('Old Blush' x *Rosa wichuriana* 'Thornless')] x 'Miracle on the Hudson'

The seeds resulting from the above pollination were stratified in an artificial environment and sown into trays in a greenhouse environment. Seedlings were obtained and displayed phenotypic and biological variation. Selective trialing and evaluation of the seedlings resulted in the identification of a single plant of the new variety.

It was found that the new shrub rose plant of the present invention possesses the following combination of characteristics:

(a) abundantly, substantially, and continuously forms large single coral pink colored blooms,
(b) exhibits a bushy and round growth habit,
(c) exhibits an exceptionally fast growth rate,
(d) forms disease resistant foliage with a smooth and glossy finish,
(e) is well suited for growing as fast growing, attractive ornamentation and a source of fragrance in in the landscape.

The new rose can be readily distinguished from its ancestors upon inspecting the blossoms and stems. More specifically, the '1000 Wishes' variety forms dissimilar coral-pink blossoms and a reduced prickle count when compared to the parental variety, 'Miracle on the Hudson'. The 'Miracle on the Hudson' variety forms dissimilar deep red blossoms and has a higher prickle count on the stems when compared to the new variety. Additionally, the new variety can be readily distinguished from its ancestors upon inspecting the base of the petals. The parental variety ['Bucbi' x ('Old Blush' x *Rosa wichuriana* 'Thornless')] forms a basal spot while the new variety is dissimilar in that it has an absence of a basal spot.

The new variety of the present invention also can be readily distinguished from other shrub rose plants, including the 'Radrazz' variety (U.S. Plant Pat. No. 11,836) upon inspection of the blossoms. For example, the 'Radrazz' variety forms dissimilar cherry-red colored blossoms.

Asexual reproduction of '1000 Wishes' was done by taking cuttings in Brenham Tex., U.S.A. in beginning in 2019. Cuttings were taken from mature stems that were approximately 10 to 15 cm in length and approximately 0.75 cm in diameter. Initial cuttings were taken of the new variety and grew into mature plants. Subsequent cuttings were taken of the initial asexually reproduced plants and grown into mature plants. Mature plants of both the initially propagated plants and the subsequently propagated plants were compared. There was no observable difference between the generations. Therefore, it was demonstrated that the characteristics of '1000 Wishes' remain stable, uniform and true to type in successive generations of asexual reproduction.

BRIEF DESCRIPTION OF THE DRAWING

The accompanying color illustration shows as true is as is reasonably possible to obtain in color photographs of this type, the typical characteristics of the plant parts, i.e., the flowers, buds, stems and leaves of the new rose, '1000 Wishes'. The illustrated rose plant parts were approximately one year of age and were observed during August, while growing on their own roots in Brenham, Tex., U.S.A. Flowers, buds, and stem growth are displayed in various stages of maturity. The upper side and under side of the leaves, blooms and petals are displayed.

DETAILED BOTANICAL DESCRIPTION

The chart used in the identification of colors is The Royal Horticultural Society Colour Chart (R.H.S. Colour Chart) Edition V. The description is based one year old specimens of the new variety during August while growing outdoors on their own roots at Brenham, Tex., U.S.A.

Class: Landscape Shrub Rose. Cultivar '1000 Wishes'.

Plant:

*Height*.—Approximately 1.1 m on average at maturity.

*Width*.—Approximately 1.1 m on average at maturity.

*Habit*.—Shrub-like, erect.

Stems:

*Size*.—Approximately 110 cm tall by 1 cm in caliper.

*Color*.—Immature: Turquoise-Green Group N144A. Mature: In between turquoise-Green Group 143A to 143B.

*Prickles*.—Size: Approximately 1.1 cm in length on average. Quantity: Sparse. Color: Turquoise-Green Group 144A. Shape: Declining Density: Irregularly spaced throughout the stems.

*Texture*.—Smooth.

*Internodal spacing*.—Approximately 6 cm on average.

Leaves:

*Arrangement*.—Alternate, odd-pinnate, and compound.

*Margin*.—Doubly serrate.

*Stipules*.—Size: Approximately 1.8 cm×1 cm on average. Margin: Adnate, revolute, and gland-ciliate edges. Color: Turquoise-Green Group 140A. Texture: Smooth.

*Size*.—Approximately 15.5 cm×10 cm on average.

*Petioles*.—Color upper surface: Turquoise-Green Group 140A. Color under surface: Turquoise-Green Group 140B. Size: Approximately 6 cm×1 mm on average. Shape: Filiform.

*Rachis*.—Color: Turquoise-Green Group 140B.

*Leaflets*.—Number: 5 and 7. Shape: Ovate. Size: Approximately 5 cm×3.5 cm on average. Venation: Reticulate Venation Color: Turquoise-Green Group 140A. Apex: Cuspidate. Base: Obovate. Texture Upper Surface: Smooth. Texture Under Surface: Matte. Overall Appearance: Medium-Green and slightly glossy. Color (Young Foliage) Upper Surface: Brown-Grey Group N199A. Color (Young Foliage) Under Surface: Yellow-Red Group 46A. Color (Adult Foliage) Upper Surface: Turquoise-Green Group 141B. Color (Adult Foliage) Under Surface: Turquoise-Green Group 143B.

Inflorescence:

*Average size of inflorescence*.—Approximately 9 cm×6 cm on average.

*Number of flowers per inflorescence*.—Approximately 3 to 5 on average.

*Florescence type*.—Cymose.

*Peduncle*.—Color: Turquoise-Green Group 143B. Length: Approximately 3.5 cm on average. Diameter: Approximately 2 mm on average. Texture: Slightly pubescent and gland-ciliate.

*Sepals*.—Number: 5 Size: Approximately 2.5 cm×0.6 cm on average. Arrangement: Pentamerous and imbricate. Shape: Obcunate. Margin: Lacinate. Apex: Spatulate to foliaceous. Base: Truncate. Texture: Glabrous. Color Upper Surface: Turquoise-Green Group 144A. Color Under Surface: Turquoise-Green Group 144A.

*Buds*.—Shape: Ovoid. Size: Approximately 2.5 cm to 1 cm on average. Color (When Opening) Inner Surface: Yellow-Red Group 46A. Color (When Opening) Outer Surface: Yellow-Red Group 53A.

Flower:

*Form*.—Single.

*Diameter*.—Approximately 8.5 cm on average.

*Color*.—(When Opening) Upper Surface: Yellow-Red Group 45B. (When Opening) Under Surface: Yellow-Red Group 46A. (When Blooming) Upper Surface: Yellow-Red Group 45B. (When Blooming) Under Surface: Yellow-Red Group 46A. (End Of Blooming) Upper Surface: Yellow-Red Group 39B. (End Of Blooming) Under Surface: Yellow-Red Group 51A to 51B.

*Fragrance*.—Slight tea and fruity fragrance.

*Petal form*.—Obchordate.

*Petals*.—Size: Approximately 4.4 cm×3.75 cm on average. Margins: Entire. Apex: Acute. Base: Subchordate. Texture: Smooth. Number: Approximately 5 to 6 on average, none of which are petaloids. Petaloids: None present. Petal Drop: Easily and cleanly after blooming.

*Stamen number*.—Approximately 105 on average.

*Anther color*.—Yellow-Red Group 34A.

*Anther shape*.—Sagittate base with rounded apex.

*Anther length*.—Approximately 1.75 mm on average.

*Filament color*.—Yellow-Red Group 14A to 14B.

*Filament length*.—Approximately 6 mm on average.

*Pollen quantity*.—Average amount of pollen produced.

*Pollen color*.—Yellow-Red Group 9A.

*Pistil form*.—Separate, free and exerted.

*Pistil number*.—Approximately 25 on average.

*Stigma color*.—Yellow-Red Group 25D.

*Style color*.—Yellow-Red Group N34A.

*Style length*.—Approximately 6 mm on average.

*Receptacle*.—Globose. Achenes form on the inside of the fruit. Size: Approximately 1 cm×1 cm on average when mature.

*Rate of flower opening*.—Fast.

*Lasting quality*.—On plant: Approximately 2 to 3 days on average. In vase: Unknown.

Development:

*Vegetation*.—Vigorous.

*Growth rate*.—Exceptionally fast.

*Hip/seed formation*.—Slightly below average amount of hip formation.

Root system:

*Root color*.—Yellow-Red Group 19C.

*Root habit*.—Well rounded.

Physiology:

*Disease resistance*.—Above average resistance to black spot *Diplocarpon rosae*, downy mildew *Peronospora sparsa*, powdery mildew *Podosphaera pannosa*, and *Cercospora* leaf spot *Cercospora rosicola*.

*Cold hardiness*.—The variety has been found to be suitable for climactic conditions in USDA Plant Hardiness Zone 8. Based on the performance of its parent varieties, it is likely, although untested, that the new variety is also suitable for climatic conditions of USDA Plant Hardiness Zones 6 and 7.

*Heat tolerance*.—The new variety exhibits above average heat tolerance, as blooms do not reduce in size, when temperatures are in excess of 100° F., as compared to other varieties 'Bucbi' and 'Old Blush' which do reduce in size under the aforementioned conditions. The variety has been found to be suitable for climactic conditions in USDA Plant Hardiness Zone 8. Based on the performance of its parent varieties, it is likely, although untested, that the new variety is also suitable for climatic conditions of USDA Plant Hardiness Zone 9.

*Drought tolerance*.—The new variety exhibits above average drought tolerance as immature stems do not experience a reduction in turgor pressure when temperatures are in excess of 100° F. This is in comparison to other varieties 'Bucbi' and 'Old Blush' which do experience a reduction in turgor pressure under the aforementioned conditions.

I claim:

1. A new and distinct variety of shrub rose plant named '1000 Wishes' characterized by the following combination of characteristics:

(a) abundantly, substantially, and continuously forms large single coral pink colored blooms, (b) exhibits a bushy and round growth habit, (c) exhibits an exceptionally fast growth rate, (d) forms disease resistant foliage with a smooth and glossy finish, and (e) is well suited for growing as fast growing, attractive ornamentation and a source of fragrance in in the landscape.

substantially as illustrated and described herein the application.

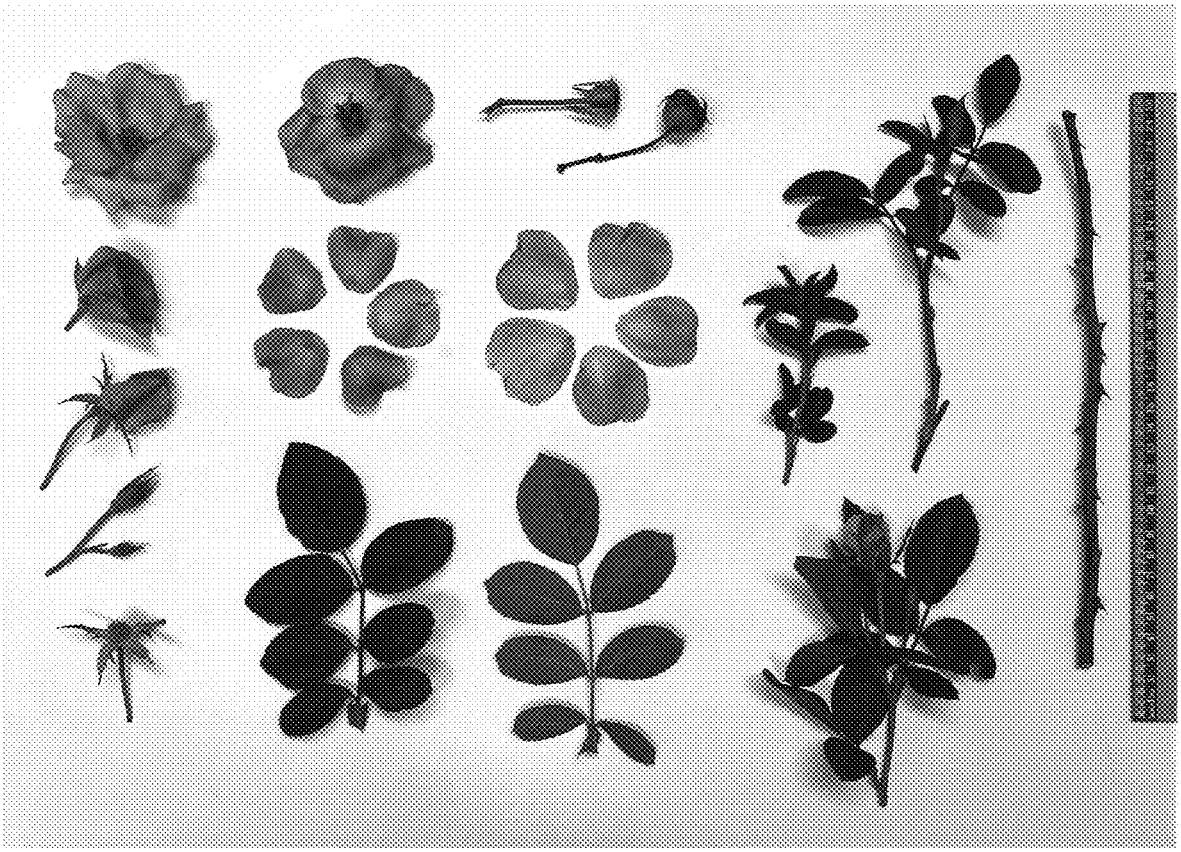

* * * * *